United States Patent
Mashiach

(10) Patent No.: US 9,220,908 B2
(45) Date of Patent: Dec. 29, 2015

(54) IMPLANT SLEEP APNEA TREATMENT DEVICE INCLUDING AN ANTENNA

(71) Applicant: Adi Mashiach, Tel Aviv, IL (US)

(72) Inventor: Adi Mashiach, Tel Aviv, IL (US)

( * ) Notice: Subject to any disclaimer, the term of this patent is extended or adjusted under 35 U.S.C. 154(b) by 0 days.

(21) Appl. No.: 14/496,212

(22) Filed: Sep. 25, 2014

(65) Prior Publication Data

US 2015/0073508 A1    Mar. 12, 2015

Related U.S. Application Data

(62) Division of application No. 13/951,856, filed on Jul. 26, 2013, now Pat. No. 8,903,515.

(60) Provisional application No. 61/676,327, filed on Jul. 26, 2012.

(51) Int. Cl.
  *A61N 1/37* (2006.01)
  *A61N 1/372* (2006.01)
  (Continued)

(52) U.S. Cl.
  CPC ........ *A61N 1/37229* (2013.01); *A61B 17/0482* (2013.01); *A61N 1/0526* (2013.01); *A61N 1/0548* (2013.01); *A61N 1/0558* (2013.01);
  (Continued)

(58) Field of Classification Search
  CPC ........... A61N 1/37229; A61N 1/36125; A61B 2018/183; A61B 2018/1838; A61B 2018/1846; A61B 2018/1835
  USPC .............................................. 607/32, 60, 134
  See application file for complete search history.

(56) References Cited

U.S. PATENT DOCUMENTS

| 5,314,457 A | 5/1994 | Jeutter et al. |
| 6,917,833 B2 | 7/2005 | Denker et al. |

(Continued)

FOREIGN PATENT DOCUMENTS

| WO | WO2004/002572 A1 | 8/2004 |
| WO | WO2007/118194 A2 | 10/2007 |
| WO | WO2010/006218 | 1/2010 |

OTHER PUBLICATIONS

Search Report and Written Opinion for International Application No. PCT/IB13/02147, dated Apr. 8, 2014, 4 pgs.

*Primary Examiner* — Paula J Stice
(74) *Attorney, Agent, or Firm* — Finnegan, Henderson, Farabow, Garrett & Dunner LLP

(57) ABSTRACT

A sleep apnea treatment device may include a flexible carrier configured to be implanted in a body of a subject. The device may also include at least one electrode disposed on the flexible carrier, the at least one electrode being configured to modulate nerve fibers of the subject. A flexible antenna may be disposed on the flexible carrier, the flexible antenna electrically connected to the at least one electrode in a manner permitting at least some energy received by the flexible antenna to be transferred to the at least one electrode. The flexible antenna may include: at least a first conductive trace arranged on a first side of the flexible carrier, the at least a first conductive trace defining at least a first elongated space between portions thereof; and at least a second conductive trace arranged on a second side of the flexible carrier, the at least a second conductive trace defining at least a second elongated space between portions thereof, wherein the at least a first conductive trace is at least partially offset from the at least a second conductive trace such that portions of the first conductive trace overly the at least a second elongated space and wherein portions of the second conductive trace underlay the at least a first elongated space.

14 Claims, 14 Drawing Sheets

(51) Int. Cl.
  *A61N 1/05* (2006.01)
  *A61B 17/04* (2006.01)
  *A61N 1/36* (2006.01)
  *A61N 1/378* (2006.01)
  *H04B 5/00* (2006.01)
  *H02J 7/02* (2006.01)
  *A61N 1/375* (2006.01)

(52) U.S. Cl.
  CPC .......... *A61N 1/3601* (2013.01); *A61N 1/36003* (2013.01); *A61N 1/3605* (2013.01); *A61N 1/3606* (2013.01); *A61N 1/3611* (2013.01); *A61N 1/36071* (2013.01); *A61N 1/36075* (2013.01); *A61N 1/36117* (2013.01); *A61N 1/36125* (2013.01); *A61N 1/36132* (2013.01); *A61N 1/36189* (2013.01); *A61N 1/375* (2013.01); *A61N 1/3787* (2013.01); *H02J 7/025* (2013.01); *H04B 5/0037* (2013.01); *H04B 5/0031* (2013.01); *H04B 5/0081* (2013.01); *H04B 5/0093* (2013.01); *Y10T 29/49018* (2015.01)

(56) References Cited

U.S. PATENT DOCUMENTS

| | | | |
|---|---|---|---|
| 7,452,334 B2 | 11/2008 | Gianchandani et al. | |
| 7,967,439 B2 | 6/2011 | Shelhamer et al. | |
| 7,973,722 B1 | 7/2011 | Hill | |
| 8,170,680 B2 | 5/2012 | Ameri | |
| 8,233,985 B2 | 7/2012 | Bulkes et al. | |
| 8,311,645 B2 | 11/2012 | Bolea et al. | |
| 8,340,780 B2 | 12/2012 | Hastings et al. | |
| 2004/0010296 A1* | 1/2004 | Swanson et al. | 607/36 |
| 2004/0171355 A1 | 9/2004 | Yu et al. | |
| 2006/0122473 A1* | 6/2006 | Kill et al. | 600/300 |
| 2006/0206185 A1 | 9/2006 | Schuller | |
| 2007/0233204 A1* | 10/2007 | Lima et al. | 607/46 |
| 2008/0132986 A1 | 6/2008 | Gray et al. | |
| 2008/0243218 A1 | 10/2008 | Bottomley et al. | |
| 2008/0262584 A1 | 10/2008 | Bottomley et al. | |
| 2009/0054952 A1 | 2/2009 | Glukhovsky et al. | |
| 2009/0157147 A1 | 6/2009 | Cauller et al. | |
| 2010/0241195 A1 | 9/2010 | Meadows | |
| 2010/0280568 A1 | 11/2010 | Bulkes et al. | |
| 2011/0009924 A1 | 1/2011 | Meskens | |
| 2011/0190849 A1 | 8/2011 | Faltys et al. | |
| 2011/0202041 A1 | 8/2011 | Forsell | |
| 2012/0095744 A1 | 4/2012 | Rahman et al. | |
| 2012/0130206 A1 | 5/2012 | Vajha et al. | |
| 2012/0296271 A1 | 11/2012 | Yomtov et al. | |
| 2013/0006326 A1 | 1/2013 | Ackermann et al. | |
| 2013/0316180 A1* | 11/2013 | Ko et al. | 428/414 |
| 2014/0031892 A1 | 1/2014 | Mashiach | |
| 2014/0031914 A1 | 1/2014 | Mashiach | |

* cited by examiner

IMPLANT SLEEP APNEA TREATMENT DEVICE INCLUDING AN ANTENNA

RELATED APPLICATIONS

The present application is a divisional of application Ser. No. 13/951,856, filed on Jul. 26, 2013, which is now U.S. Pat. No. 8,903,515, issued on Dec. 2, 2014, and which claims the benefit of U.S. Provisional Patent Application No. 61/676,327, filed on Jul. 26, 2012, the entire disclosures of which are hereby incorporated by reference.

TECHNICAL FIELD

The present disclosure relates to an implanted sleep apnea treatment device for modulating a nerve and methods for manufacturing the same. More particularly, embodiments of the present disclosure relate to an antenna component in an implantable unit.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure.

Among the conditions to which neural modulation may be applied is obstructive sleep apnea (OSA). OSA is a respiratory disorder characterized by recurrent episodes of partial or complete obstruction of the upper airway during sleep. During the sleep of a person with OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

Some embodiments may include a sleep apnea treatment device having a flexible carrier configured to be implanted in a body of a subject. The device may also include at least one electrode disposed on the flexible carrier, the at least one electrode being configured to modulate nerve fibers of the subject. A flexible antenna may be disposed on the flexible carrier, the flexible antenna electrically connected to the at least one electrode in a manner permitting at least some energy received by the flexible antenna to be transferred to the at least one electrode. The flexible antenna may include: at least a first conductive trace arranged on a first side of the flexible carrier, the at least a first conductive trace defining at least a first elongated space between portions thereof; and at least a second conductive trace arranged on a second side of the flexible carrier, the at least a second conductive trace defining at least a second elongated space between portions thereof, wherein the at least a first conductive trace is at least partially offset from the at least a second conductive trace such that portions of the first conductive trace overly the at least a second elongated space and wherein portions of the second conductive trace underlay the at least a first elongated space.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may include providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with OSA, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

Although the present disclosure is being initially described in the context of treatment of OSA through modulating nerve, the present sleep apnea treatment device may be employed in any patient/portion of a body where nerve modulation may be desire. That is, in addition to use in patients with migraine headaches, or hypertension, embodiments of the present disclosure may be use in many other areas, including, but not limited to: deep brain stimulation (e.g., treatment of epilepsy, Parkinson's, and depression), cardiac pace-making, stomach muscle stimulation (e.g., treatment of obesity), back pain, incontinence, menstrual pain, and/or any other condition that may be affected by neural modulation.

Figure 1:
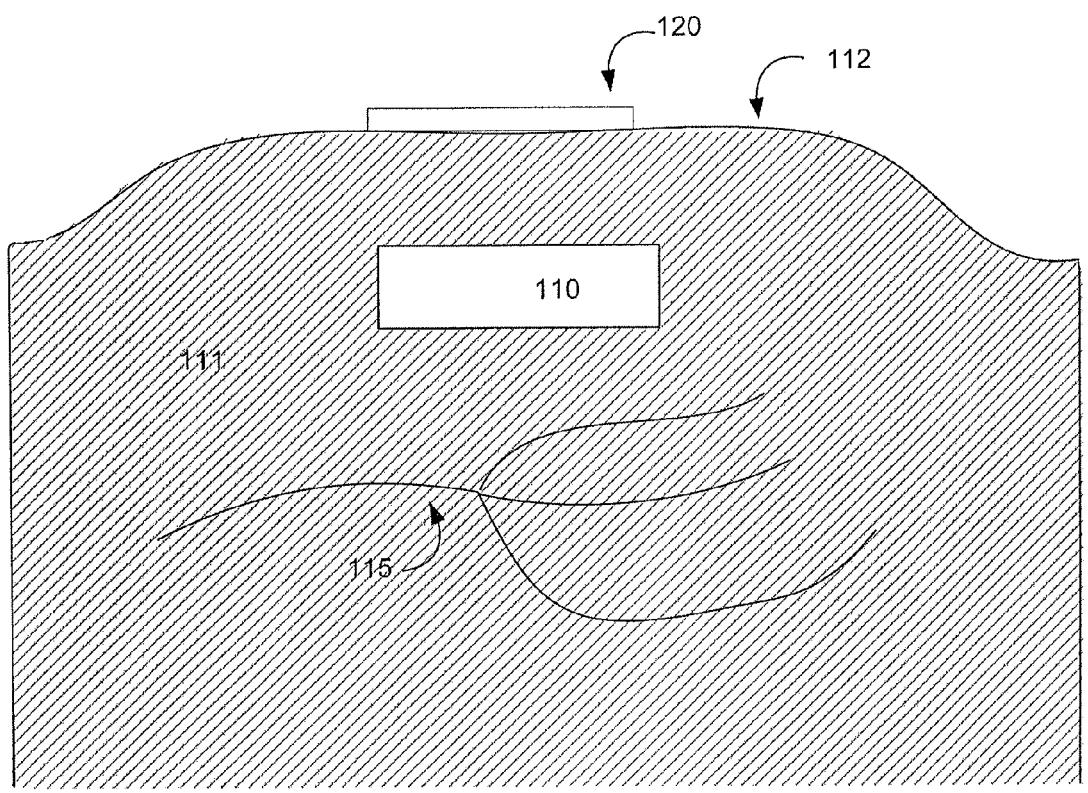
FIG. 1 schematically illustrates an implant unit and external unit, according to an exemplary embodiment of the present disclosure.

A medical system for transmitting energy to an implant sleep apnea treatment device for neuromodulation may include an implant sleep apnea treatment device and external sleep apnea treatment device. For example, FIG. 1 illustrates an implant unit 110 and an external unit 120, according to an exemplary embodiment of the present disclosure. Implant unit 110 may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists.

In treating OSA, implant unit 110 may be located on a genioglossus muscle of a patient. Such a location is suitable for modulation of the hypoglossal nerve, branches of which run inside the genioglossus muscle. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Implant unit 110 may include a flexible carrier configured to be implanted into a body of a subject. Implant unit 110 may further be configured to conform to and anchor to tissue in the subject's body. Implant unit 110 may include various components such as, for example, a flexible carrier, at least one electrode disposed on the flexible carrier and configured to modulate a nerve in the subject's body, and a flexible antenna comprising first and a second conductive traces disposed on first and second sides of the flexible carrier.

Figure 4:
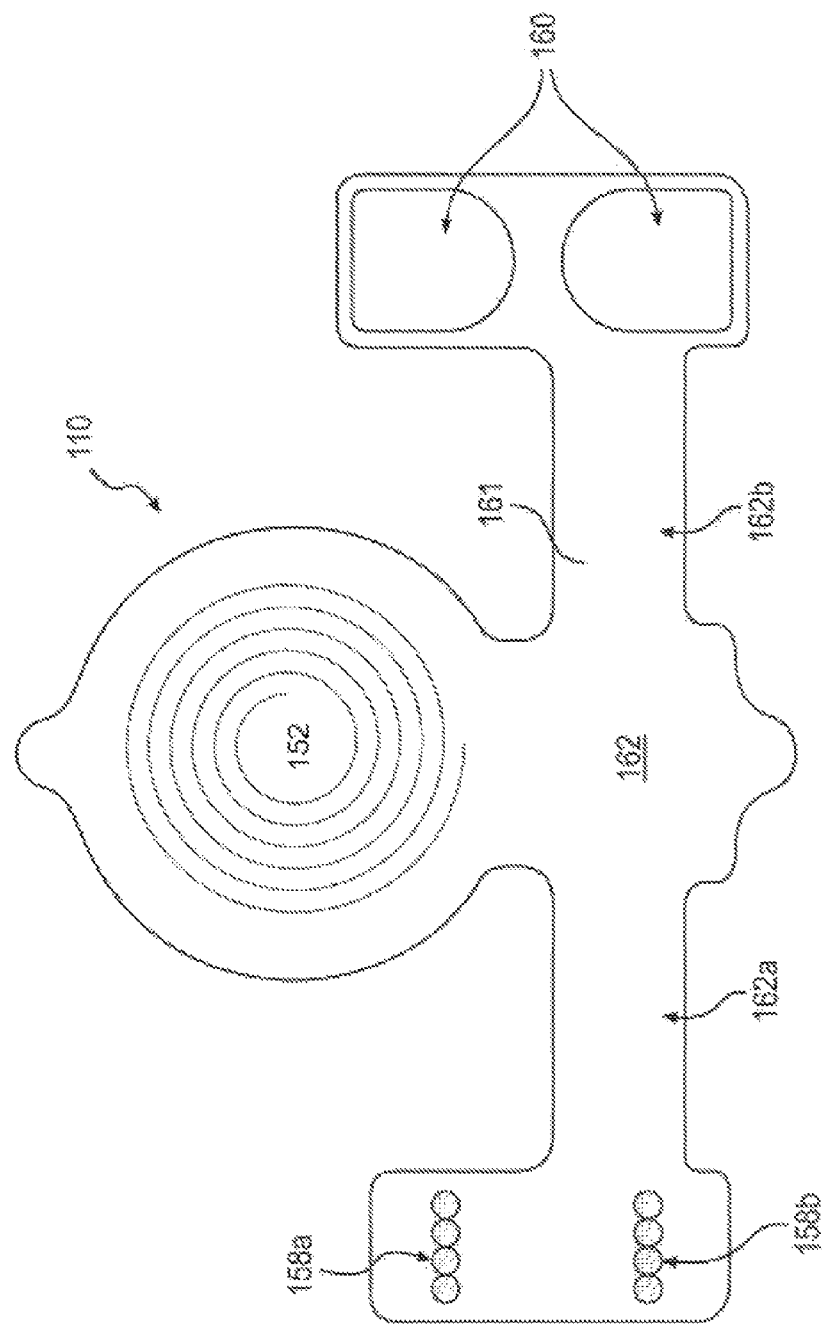
FIG. 4 is a top view of an implant unit, according to an exemplary embodiment of the present disclosure.

FIG. 4 is a top view of an implant unit, according to an exemplary embodiment of the present disclosure. Implant unit 110 includes a flexible carrier 161, electrodes 158a and 158b, and a flexible antenna 152. The term flexible refer to a capability of a component to change its physical shape (e.g., bend, flex, deform, etc.) while maintaining its desired functionality. In some embodiments, flexible antenna 152, for example, may be configured to conform to tissue (e.g., bone, muscle, adipose, connective, etc.) in the subject's body.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Implant unit 110 may additionally include a plurality of field-generating implant electrodes 158a, 158b, which may include any suitable shape and/or orientation on the implant unit so long as the electrodes may be configured to generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 5. Implant electrodes may have a thickness between about 200 nanometers and 1 millimeter. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm to 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm to 1 mm.

As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. Additionally, or alternatively, implant unit 110 may include surgical mesh 1050 or other perforatable material, described in greater detail below with respect to FIG. 10. In some embodiments, implant unit may appear substantially as illustrated in FIG. 4. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body.

As illustrated in FIG. 4, secondary antenna 152 and electrodes 158a, 158b may be mounted on or integrated with flexible carrier 161. Various circuit components and connecting wires (discussed further below) may be used to connect secondary antenna with implant electrodes 158a and 158b in a manner permitting the antenna to transfer at least some of the energy received at the antenna (e.g., from a unit including a primary antenna located external to the body of the subject) to one or more of electrodes 158a, 158b. Other components that may be included in or otherwise associated with circuitry connecting secondary antenna 152 with electrodes 158a and 158b may include, for example, modifier circuit 154, diode 156, sensor (not shown), etc.

To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers.

Figure 5:
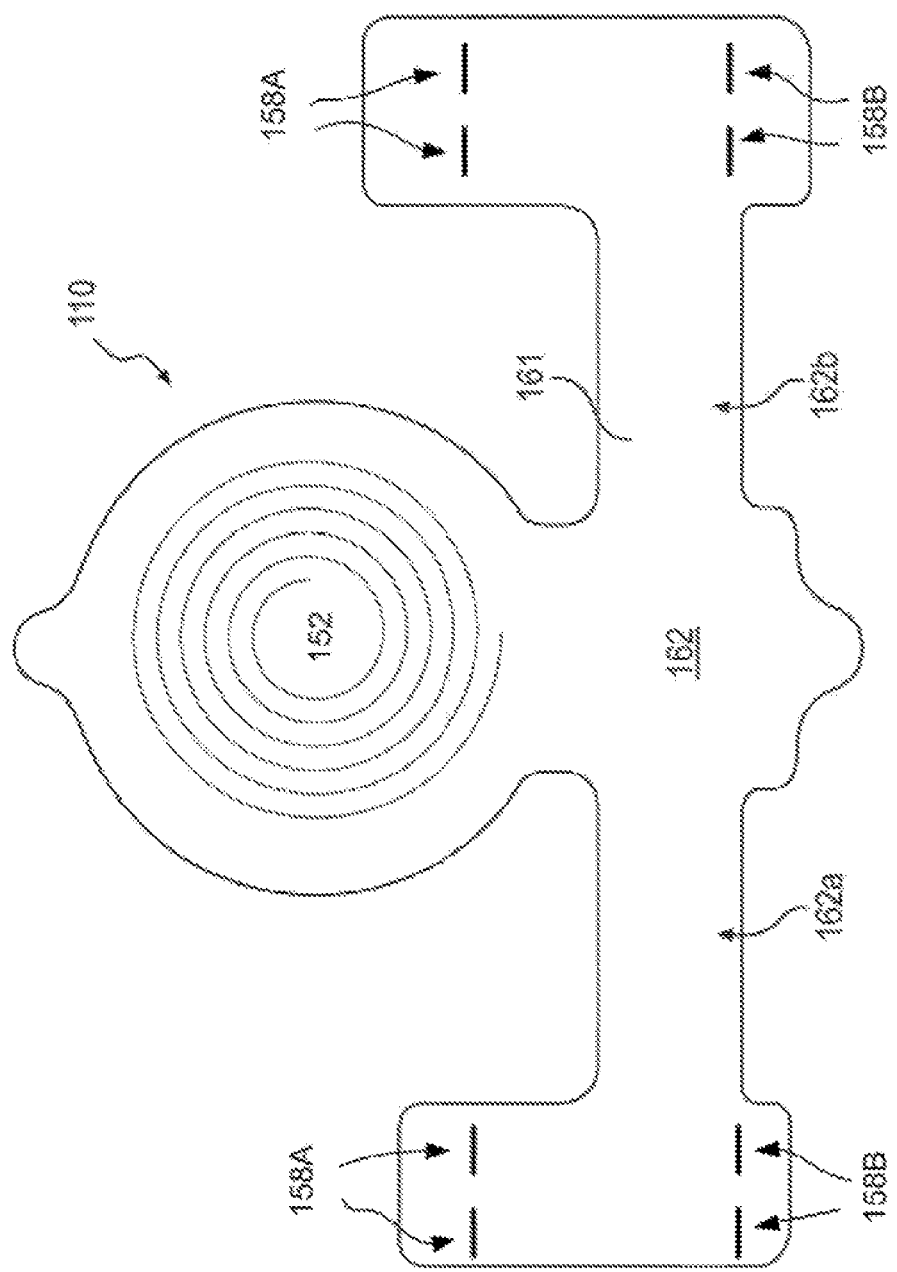
FIG. 5 is a top view of an alternate embodiment of an implant unit, according to an exemplary embodiment of the present disclosure.

FIG. 5 is a perspective view of an alternate embodiment of an implant unit 110, according to an exemplary embodiment of the present disclosure. As illustrated in FIG. 5, implant unit 110 may include a plurality of electrodes, located, for example, at the ends of first extension 162a and second extension 162b. FIG. 5 illustrates an embodiment wherein implant electrodes 158a and 158b include short line electrodes.

In some embodiments of the present disclosure, secondary antenna 152 may be disposed on flexible carrier 161 and may include a double layer trace configuration. The term "antenna" herein and throughout of the specification refers to any component that is configured to wirelessly transmit and/or receive electrical energy. The terms "trace" or "conductive trace" as used herein and throughout the specification may include any electrically conductive line, via, coil, etc.

Arranging an antenna coils in a double layer may serve to increase the transmission range of the antenna without increasing the size of the antenna. Such an arrangement, however, may also serve to increase capacitance between the wires of each coil. In each wire coil, an amount of parasitic capacitance between wires may partially depend on the distance each wire is from its neighbor. In a single layer coil, capacitance may be generated between each loop of the coil and its neighbors to either side. Thus, more compact coils may generate more parasitic capacitance. When a second layer coil is added, additional capacitance may then be generated between the wires of the first coil and the wires of the second coil. This additional capacitance may be further increased if corresponding loops of the first and second coils have the same or similar diameters, and/or if a flexible, dielectric carrier separating the loops is made very thin. Increased parasitic capacitance in an antenna may serve to alter characteristics, such as resonant frequency, of the antenna in unpredictable amounts based on manufacturing specifications. Additionally, resonant frequency drift, caused, for example by moisture incursion or antenna flexing, may be increased by the presence of increased parasitic capacitance. Thus, in order to decrease variability in the manufactured product, it may be advantageous to reduce the levels of parasitic capacitance in a dual layer antenna.

In some embodiments, for example, secondary antenna 152 may include any suitable shape. For example, in some embodiments, antenna 152 may include a coil antenna configured to include conductive traces having rectangular windings (e.g., one or more turns of a conductive trace), circular windings, oval-shaped windings, web-shaped windings, etc. Antenna 152 may also be made from any suitable conductive material and may be configured to include any suitable diameter, number of coils, layout of coils, etc. For example, a coil antenna suitable for use as secondary antenna 152 may have a diameter of between about 0.5 mm and 30 mm, and may be circular or oval shaped, or any other suitable shape. A coil antenna suitable for use as a secondary antenna 152 may have any number of windings, e.g. 4, 15, 20, 30, or 50. A coil antenna suitable for use as secondary antenna 152 may have a wire diameter between about 0.001 mm and about 1 mm. In some embodiments, secondary antenna 152 may include a flexible coil enabling the antenna to conform to contours of tissue inside of a patient's body. These antenna parameters are exemplary only, and may be adjusted above or below the ranges given to achieve suitable results. In certain embodiments, as noted above, the windings may refer to one or more turns of conductive trace. Such windings in antenna 152 may be arranged in an elliptical shape or any other shape such as circular, oval, rectangular, triangular, square, web shaped, mesh shaped, etc. In some embodiments of the present disclosure, antenna 152 may include flexible windings.

The conductive traces of antenna 152 or any other antenna disclosed herein, in addition to have the shapes and configurations described above, may be arranged in any other configuration suitable for providing an antenna. For example, the conductive traces may be arranged in linear sections, arced sections, multi-sided sections, wavelike patterns, etc. Each embodiment may include at least one elongated space formed between traces of the antenna.

In some embodiments, antenna 152 may include a double layer crossover antenna having a first electrically conductive trace arranged on a first side of a flexible dielectric carrier. In some embodiments, the first electrically conductive trace defines a first elongated space between portions thereof. For example, in some embodiments, the elongated space may include spaces between a series of progressively larger windings disposed relative to a center of antenna 152. The first elongated space, however, may also include any other shape or configuration depending on the shape or configuration of the first electrically conductive trace. In the case of circular windings, shown in FIG. 11b, first elongated space 1109 may include spaces between substantially concentric windings.

Antenna 152 may also include a second electrically conductive trace arranged on second side of flexible dielectric carrier 161. In some embodiments, the second electrically conductive trace may define a second elongated space between portions thereof. For example, like in the first electrically conductive trace, the elongated space formed by the second electrically conductive trace, in at least some cases, may include spaces between a series of progressively larger windings disposed relative to a center of antenna 152. The second elongated space, however, may also include any other shape or configuration depending on the shape or configuration of the second electrically conductive trace. In the case of circular windings, the second elongated space may include spaces between substantially concentric windings.

In some embodiments, the first conductive trace may be at least partially offset from the second conductive trace. In such embodiments, portions of the first conductive trace may overlay at least a portion of the second elongated space formed by the second conductive trace. Similarly, portions of the second conductive trace may lie under the elongated space formed by the first conductive trace.

The first and second conductive traces may include any suitable amount of offset. For example, in some embodiments, the first and second conductive trances may be partially offset such that only some of the first conductive trace or portions of the first conductive trace overlay the at least a second elongated space formed by the second conductive trace, and wherein only a portion of the second conductive trace underlays the first elongated space formed by the first conductive trace. Alternatively, in some embodiments, the first and second conductive traces may be fully offset such that substantially all of the first conductive trace overlies the elongated space formed by the second conductive trace, and substantially all of the second conductive trace underlays the elongated space formed by the first conductive trace.

Figure 11A:
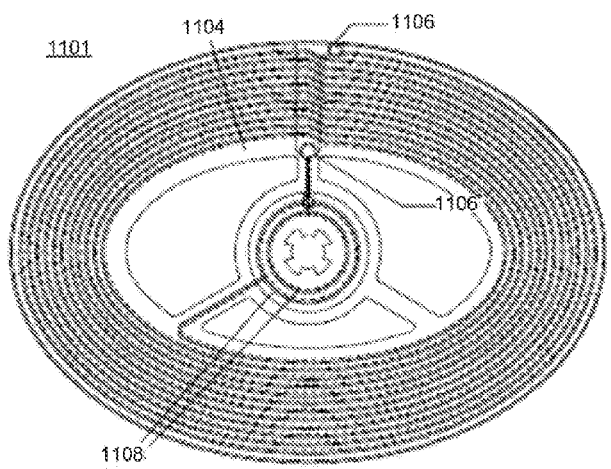
FIGS. 11a and 11b illustrate a double-layer crossover antenna.
Figure 11B:
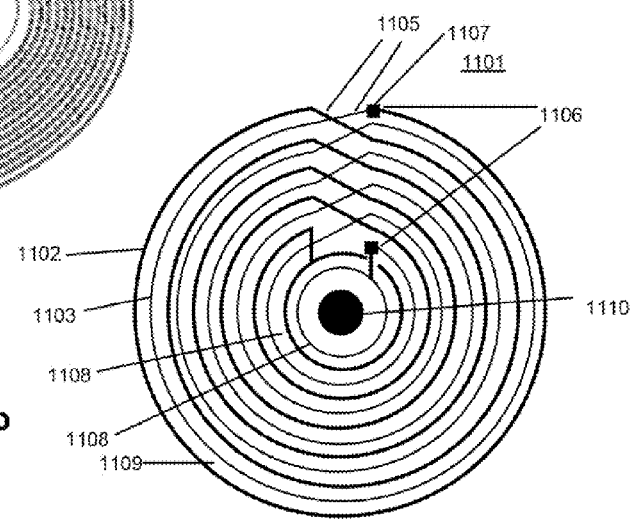

FIGS. 11a and 11b illustrate an exemplary double-layer crossover antenna 1101 suitable for use as secondary antenna 152. While a crossover pattern is shown, other patterns may also be suitable. For example, in some embodiments, a wire associated with secondary antenna 152 may include a pattern of traces of progressively decreasing dimension. In the case of traces arranged in coils, for example, each loop could include rings of progressively decreasing diameter to create a pattern that spirals inwardly. A similar approach may be viable using traces of other shapes as well.

FIG. 11a, illustrates a single coil of double-layer crossover antenna 1101, while FIG. 11b illustrates two layers of double layer crossover antenna 1101. Antenna 1101 may include a first coil of wire 1102 arranged on a first side of a flexible dielectric carrier 1104 (not shown) and a second coil of wire 1103 on a second side of a flexible dielectric carrier 1104 (not shown).

In some embodiments, antenna 152 may include a single layer or a double layer, as shown in FIGS. 11a and 11b, respectively. In other embodiments, antenna 152 may include a different numbers of layers. For example, antenna 152 may include three layers, four layers, or more. In such embodiments, respective traces on the various layers may be separated by an insulating layer and may be configured relative to one another in a manner similar to the relative configurations of the first and second conductive traces described above.

Figure 11C:
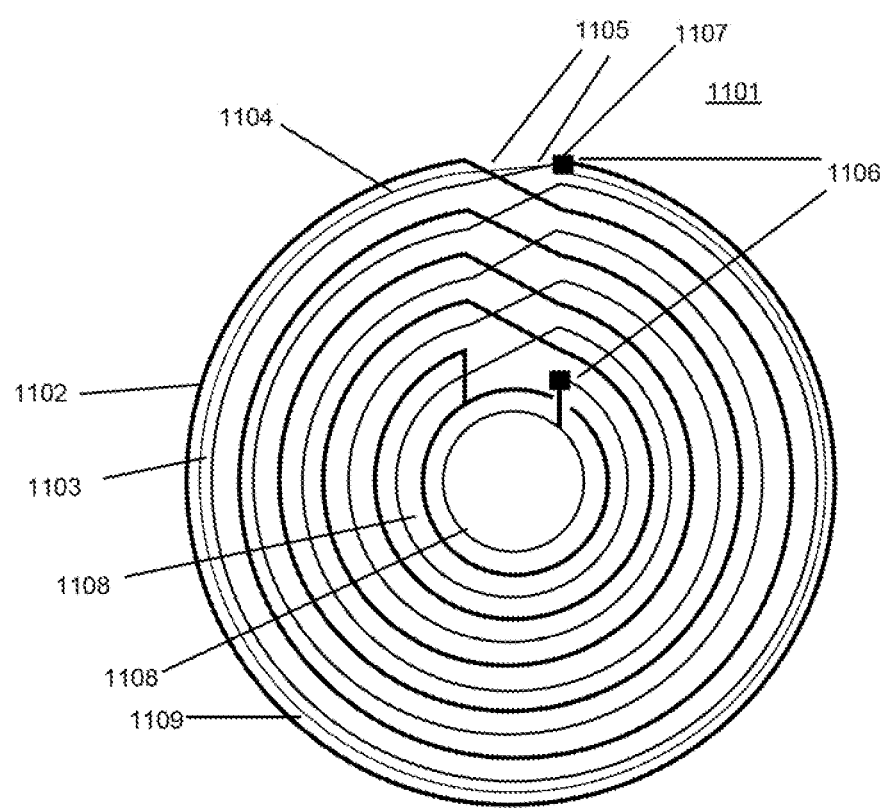
FIG. 11c illustrates additional features of embodiment of a double-layer cross-over antenna.
Figure 11D:
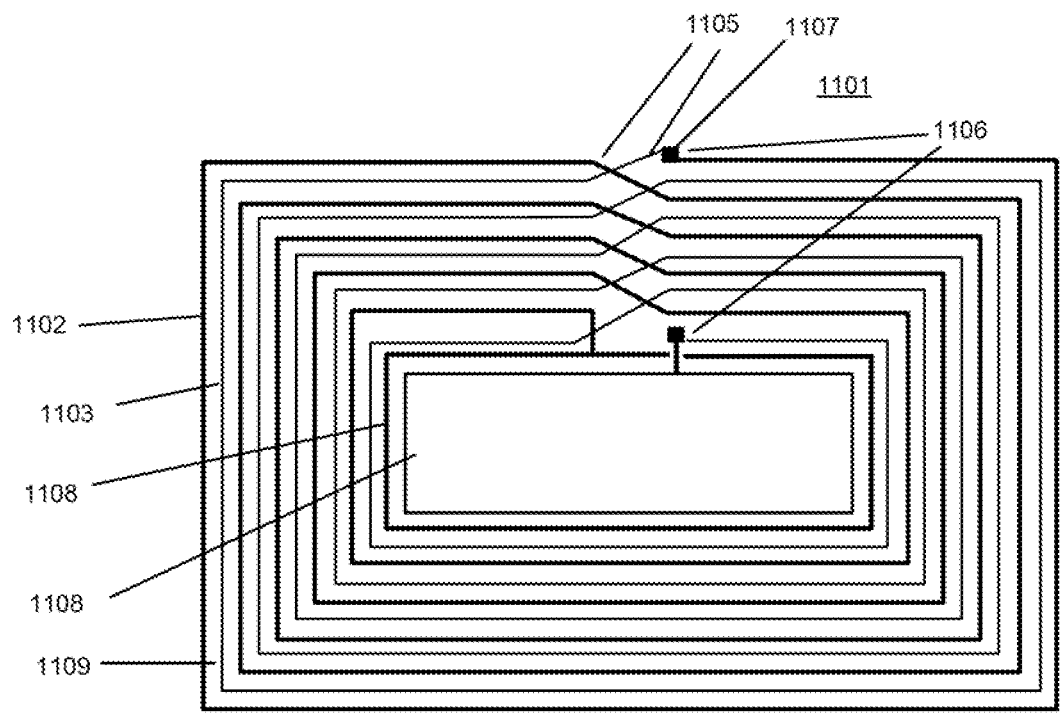
FIG. 11d illustrates another embodiment of a double layer cross-over antenna.

FIG. 11b illustrates a double layer crossover antenna 1101. Such a configuration may serve to reduce the parasitic capacitance in a manufactured antenna. As illustrated in FIG. 11b, a first coil of wire 1102 may be concentrically offset from a second coil of wire 1103. In contrast to a configuration where each loop of a first coil 1102 has the same diameter as corresponding loop of the second coil 1103, concentrically offsetting corresponding loops of each wire coil may serve to increase the distance between a single loop of the first coil 1102 with a corresponding loop of the second coil 1103. This increased distance, in turn, may decrease the parasitic wire-to-wire capacitance between loops of first coil 1102 and corresponding loops of second coil 1103. This configuration may be particularly advantageous in reducing parasitic capacitance in a situation where a dielectric carrier 1104 is thin enough such that the concentric distance by which each coil is offset is relatively large compared to the thickness of the dielectric carrier 1104. For example, in a situation where a dielectric carrier is 0.5 mm thick, a concentric offset of 0.5 mm or more may produce a large change in parasitic capacitance. In contrast, in a situation where a dielectric carrier is 5 mm thick, a concentric offset of 0.5 mm may produce a smaller change in parasitic capacitance. The concentric offset between a first coil 1102 and a second coil 1103 may be achieved, for example, by a plurality of electrical trace steps 1105 that offset each loop of the coils from each preceding loop. Electrical trace steps 1105 on a first side of dielectric carrier 1104 cross over electrical trace steps 1105 on a second side of dielectric carrier 1104, thus providing the crossover feature of double-layer crossover antenna 1101. The term "electrical trace step" herein refers to any electrical connection element (e.g., trace, wire, via, etc.) that may establish electrical connectivity between two parts of a conductive trace. In some embodiments, the first conductive trace may include first windings and at least some of the first windings may be connected to one another by first electrical trace steps. Similarly, the second conductive trace may include second windings and at least some of the second windings are connected to one another by second electrical trace steps, wherein one or more of the first electrical trace steps cross one or more of the second trace steps at a non-zero angle, as shown in FIG. 11b, for example. One or more additional conductive traces may be provided. For example, in FIG. 11c, a third conductive trace 1104 is provided. It is contemplated that the third conductive trace may be spaced apart from at least the first conductive trace and the second conductive trace by an insulating layer.

Returning to FIG. 11a, in some embodiments, double layer crossover antenna 1101 may include openings 1106 in flexible carrier 1104 to facilitate the electrical connection of first and second coils 1102, 1103. In some embodiments the electrical connection between first and second conductive traces may include an electrical trace step (e.g., a conductive via) extending through holes 1107 in the flexible carrier (e.g., openings 1106) to provide an electrical connection between the first and second conductive traces. First and second coils 1102, 1103 of double layer crossover antenna 1101 may also include exposed electrical portions 1108 configured to electrically connect with a connector of a device housing that may be coupled to antenna 1101. Exposed electrical portions 1108 may be configured so as to maintain electrical contact with the connector of a device housing independent of the axial orientation of the connection. As shown in FIG. 11a, for example, exposed electrical portions 1108 may be configured as continuous or discontinuous circles in order to achieve this. A first exposed electrical portion 1108 configured as a discontinuous circle may provide a space through which an electrical trace may pass without contacting the first exposed electrical portion, for example to connect with a second exposed electrical portion located inside the first, or to other components located within the circle of the first exposed electrical portion 1108. FIG. 11a illustrates an antenna having substantially elliptical coils; other shapes, such as circular, rectangular, triangular, square, web-shaped etc., may be also be used in different embodiments. In some other embodiments, the coils winding in a flexible antenna may include a ferrite core 1110. Elliptical coils may facilitate placement in certain areas while maintaining desirable electrical performance characteristics.

Figure 10:
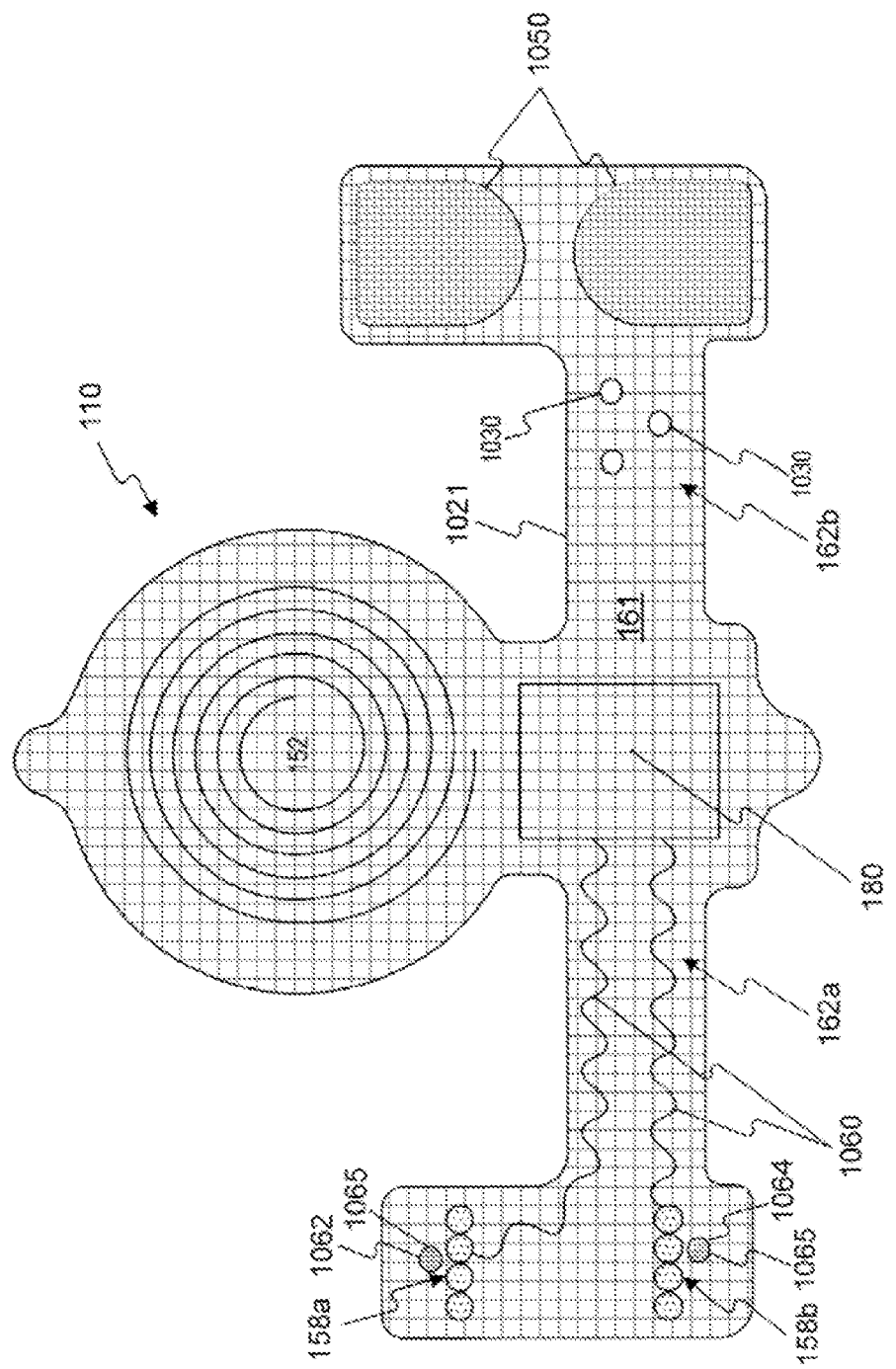
FIG. 10 illustrates additional features of one embodiment of implant unit 110.

FIG. 10 illustrates additional features of one embodiment of implant unit 110. Exemplary embodiments may incorporate some or all of the features illustrated in FIG. 10. A protective coating of implant unit 110 may include a primary capsule 1021. Primary capsule 1021 may encapsulate the implant unit 110 and may provide mechanical protection for the implant unit 110. For example, the components of implant unit 110 may be delicate, and the need to handle the implant unit 110 prior to implantation may require additional protection for the components of implant unit 110. Primary capsule 1021 may provide such protection. Primary capsule 1021 may encapsulate all or some of the components of implant unit 110. For example, primary capsule 1021 may encapsulate antenna 152, carrier 161, and circuit 180, while leaving electrodes 158a, 158b exposed. In alternative embodiments, different combinations of components may be encapsulated or exposed. Primary capsule 1021 may be fashioned of a material and thickness such that implant unit 110 remains flexible after encapsulation. Primary capsule 1021 may include any suitable bio-compatible material, such as silicone, or polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating.

Figure 12:
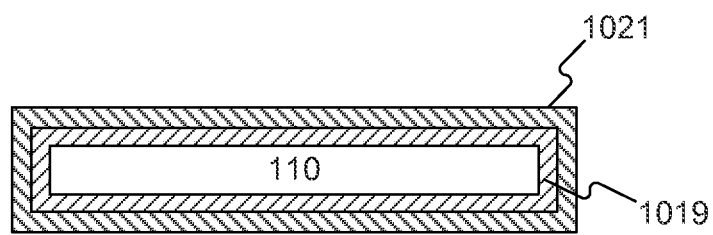
FIG. 12 illustrates a primary capsule and secondary capsule encapsulating the implant unit, according to embodiments of the invention.

The protective coating of implant unit 110 may also include a secondary capsule 1019 (FIG. 12). Secondary capsule 1019 may provide environmental protection for the implant unit 110 when it is implanted in the body. For example, primary capsule 1021, when constructed of silicone, may be subject to moisture incursion from the body, which may limit a life-span of the implant unit 110 due to possible corrosive effects. Secondary capsule 1019 may be provided underneath the primary capsule 1021 to protect implant unit 110 from the corrosive effects of bodily implantation. For example, a layer of parylene C may serve as secondary capsule 1019 and may be provided to encapsulate all or some of the components of implant unit 110. Secondary capsule 1019 may, in turn, be encapsulated by primary capsule 1021. Secondary capsule 1019, may include, for example parylene C or any other suitable material to prevent the effects of moisture incursion on implant unit 110. In some embodiments, a secondary capsule layer may be deposited by chemical vapor deposition and may have a thickness of about 1 molecule in thickness, between 1 and 5 molecules in thickness, or any other suitable film thickness.

Some combinations of primary and secondary capsule materials, such as silicone and parylene C, may bond relatively weakly to one another. Where such combinations of materials are used, a plurality penetrating holes 1030 may be provided to pass through both carrier 161 and a secondary capsule to improve the adherence of the primary capsule. When penetrating holes 1030 are provided, the material of primary capsule 1021 may flow through the penetrating holes, permitting the material of primary capsule 1021 to flow into and adhere to itself. A plurality of penetrating holes 1030 provided through carrier 161 and a secondary capsule may provide a multitude of anchor points to permit a primary capsule 1021 material to self adhere. Penetrating holes 1030 may be provided such that, after encapsulation by primary capsule 1021, the holes 1030 remain, or they may be provided such that, after encapsulation, the holes 1030 are filled in.

Also illustrated in FIG. 10 are suture holes 1050, 1062 and 1064, which may include encapsulated surgical mesh 1064 therein. Suture holes 1050 may provide a larger target area for surgeons to use when suturing implant unit 110 into place during implantation. The entire suture holes 1050 may be encapsulated by primary capsule 1021 and may permit a surgeon to pass a needle through any portion of the suture holes without compromising the integrity of implant unit 110. Surgical mesh 1064 may be used to cover suture holes 1050, permitting larger suture holes 1050 that may provide surgeons with a greater target area. Surgical mesh 1064 may also encourage surrounding tissue to bond with implant unit 110. In some embodiments, a surgeon may pass a surgical suture needle through suture holes 160, located on one extension 162a of an elongate arm 162 of implant unit 110, through tissue of the subject, and through surgical mesh 1064 provided on a second extension 162b of elongate arm 162 of implant unit 110. In this embodiment, the larger target area provided by suture holes 1050 may facilitate the suturing process because it may be easier to locate a larger suture hole after a suture needle passes first through a suture hole in extension 162a and subsequently passes through tissue in the subject's body.

Additionally, implant unit 110 may include meandering electrical traces 1060 in order to maintain electrical contact under flexural conditions. As used herein, meandering electrical traces 1060 may include any electrical trace that is longer than the shortest distance between the points that it connects. Meandering electrical traces 1060 may also include any trace of sufficient length so as to maintain electrical conductivity during flexing of a carrier on which it is located. For example, as shown in FIG. 10, meandering electrical traces 1060 may be configured as lines having successive curves, such as waves or the like. Repeated flexing of carrier 161 on which electrical traces are deposited may cause degradation of the electrical traces, as they are repeatedly stressed with the flexure of carrier 161. Meandering electrical traces 1060 may provide an increased lifetime, as the additional slack provided may serve to reduce stress in the traces during flexing of carrier 161. Meandering electrical traces 1060 may include any suitable conductive material, such as gold, platinum, titanium, copper, silver, iridium, platinum-iridium, platinum-gold, conductive polymers, any conductive biocompatible material, and/or combinations of conductive (and/or noble metals) materials.

In additional embodiments consistent with the present disclosure, conductive electrical elements of implant unit 110, such as meandering traces 1060 and electrodes 158a, 158b may be provided through a progressive metallization layering method. In some embodiments, flexible carrier 161 may include a material, such as liquid crystal polymer, that bonds relatively weakly to conductive metals desirable for use as conductive electrical elements, such as titanium and/or gold. A progressive metallization layering method may utilize a temporary bonding layer, including a metal, such as nickel, that may bond more strongly to flexible carrier 161. The temporary bonding layer may be layered with the metals desirable for use as conductive electrical elements and used to provide an initial bond with the material of flexible carrier 161. The temporary bonding layer may then be removed through dissolution, erosion, or similar technique, through flexible carrier 161, leaving the desirable metals in place in flexible carrier 161.

In one embodiment, a progressive metallization layering method may be utilized to provide gold and titanium conductive elements on a liquid crystal polymer carrier 161. The conductive elements may be constructed from progressive layers of nickel, gold, and titanium. Next, liquid crystal polymer may be molded around the conductive elements, bonding strongly with the nickel layer and forming a recess containing the layered conductive element. Finally, the nickel may be removed through the liquid crystal polymer through dissolution, erosion, or similar technique. The removal of nickel leaves the gold/titanium layered conductive element in place, held tightly in the liquid crystal polymer recess created during the molding process.

Figure 2:
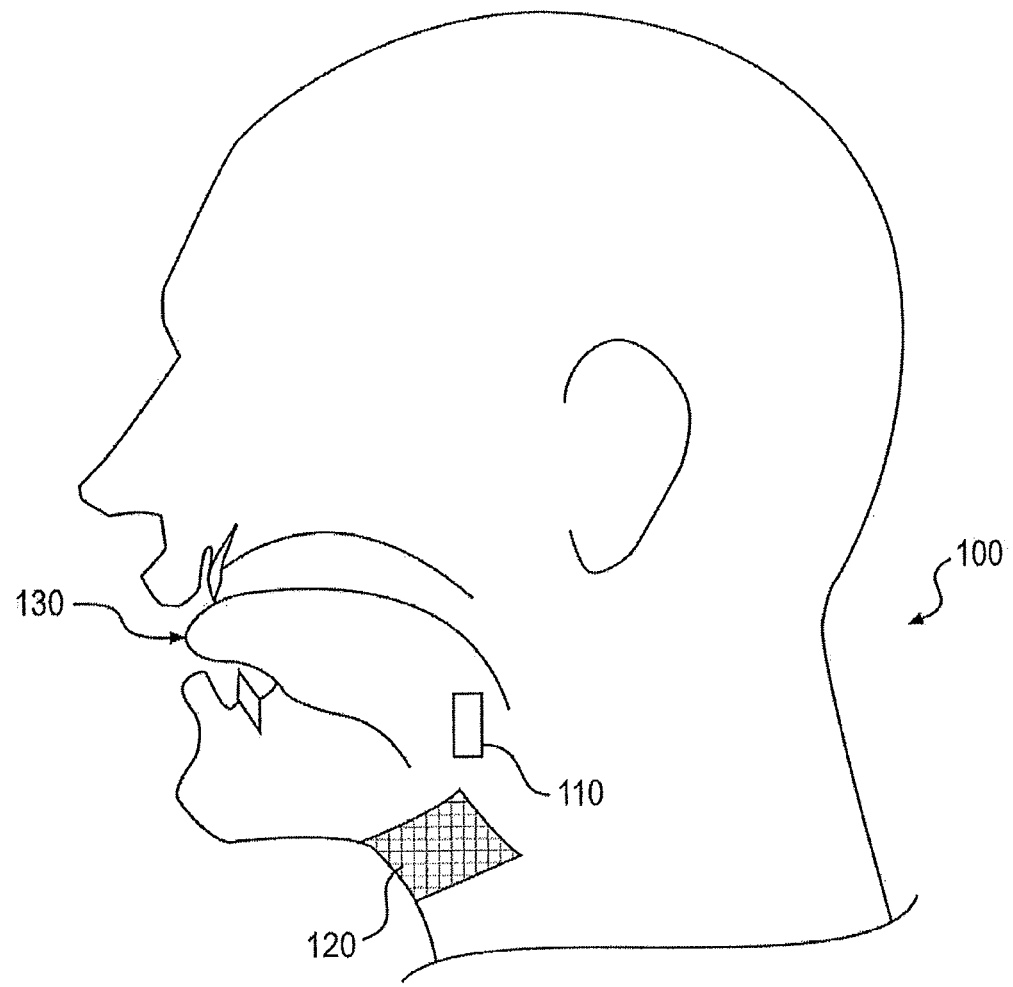
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to the patient 100. FIG. 2 illustrates that in a patient 100 with OSA, the external unit 120 may be configured for placement underneath the patient's chin and/or on the front of patient's neck. The suitability of placement locations may be determined by communication between external unit 120 and implant unit 110, discussed in greater detail below. In alternate embodiments, for the treatment of conditions other than OSA, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 120 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. In some embodiments, for example, the flexible substrate may have a thickness of between 5 to 100 micrometers (e.g. 5, 15, 50, 100 micrometers). Any portion of external unit 120 may be flexible or rigid, depending on the requirements of a particular application. For example, in treating OSA, the flexible substrate may be included in a patch sized to lie substantially within an area bounded by opposing mandibular angles and a mental tubercle with a maximum length of about 18 mm.

As previously discussed, in some embodiments external unit 120 may be configured to adhere to a desired location. Accordingly, in some embodiments, at least one surface of the flexible substrate may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
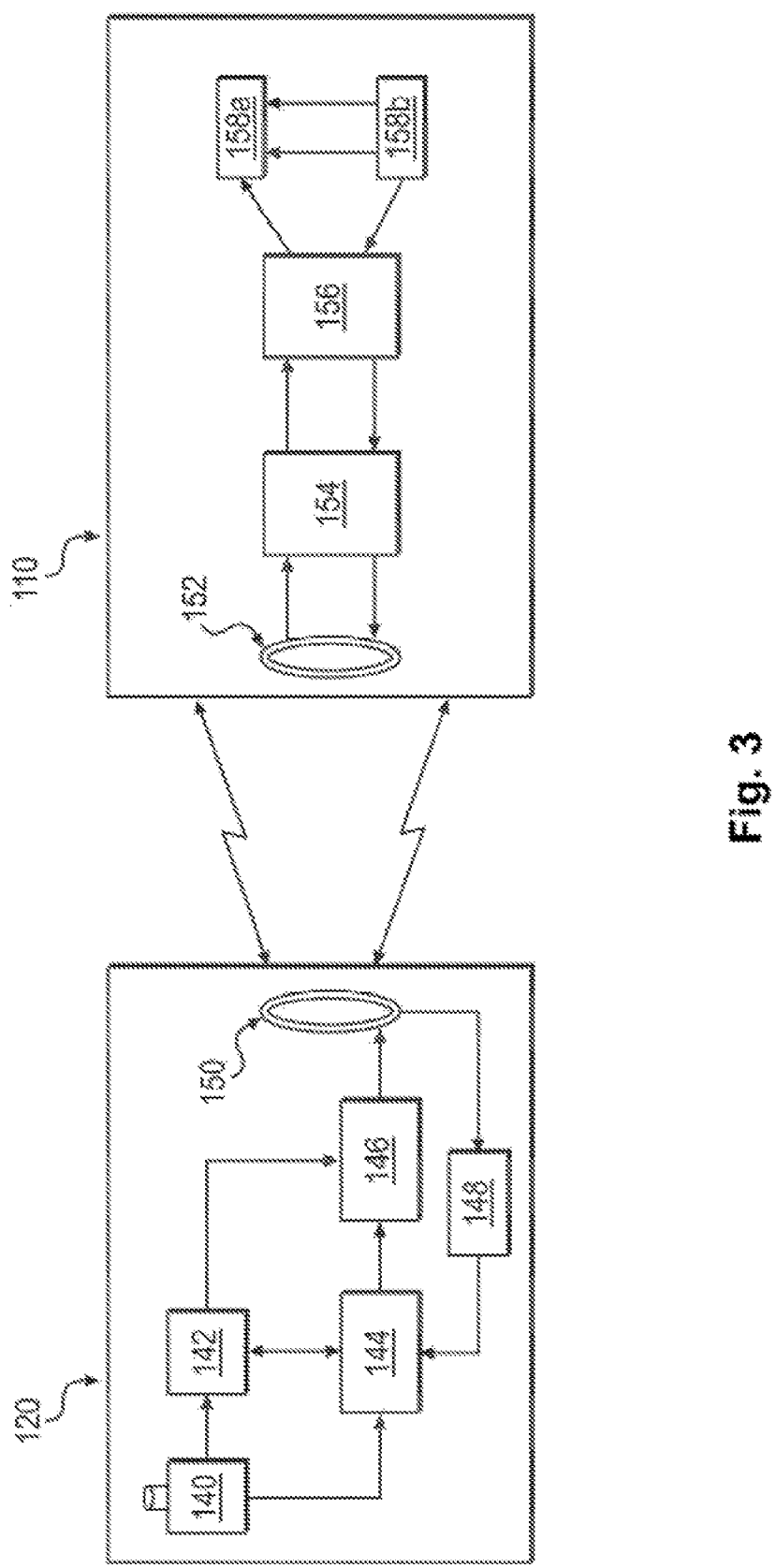
FIG. 3 schematically illustrates a system including an implant unit and an external unit, according to an exemplary embodiment of the present disclosure.

Referring to FIG. 3, internal unit 110 may be configured as a unit to be implanted into the body of a patient, and external unit 120 may be configured to send signals to and/or receive signals from implant unit 110. As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removable coupled to the external unit at an exterior location relative to external unit. Alternatively, as shown in FIG. 3, power source 140 may be permanently or removable coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.4 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. The amplifier may further be configured to output the amplified signals to one or more components within external unit 120.

The external unit may additionally include a flexible primary antenna 150. The primary antenna may be configured as part of a circuit within external unit 120 and may be coupled either directly or indirectly to various components in external unit 120. For example, as shown in FIG. 3, primary antenna 150 may be configured for communication with the amplifier 146.

In some embodiments, primary antenna 150 may include any conductive structure that may be configured to create an electromagnetic field. The primary antenna may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. In some other embodiments the primary antenna may include any suitable antenna known to those skilled in the art that may be configured to send and/or receive signals. For example, primary antenna 150 may be formed according to any of the structures and configurations described above with respect to secondary antenna 152. Suitable antennas may include, but are not limited to a single layer antenna, a double layer as illustrated in FIG. 11b, or may include three or more layers. Antenna 150 may also include a coil antenna, a long-wire antenna, a patch antenna, a helical antenna, etc. In some embodiments of the present disclosure, primary antenna 150 may have a transmission frequency of between 6.4 to 8.3 MHz, and may be configured to transmit energy to a penetration depth of at least 1 cm into a patient's body.

In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 0.5 cm and 15 cm, and may be circular or oval shaped or any other suitable shape. In some embodiments, a coil antenna may have a diameter between 5 cm and 7 cm, and may be oval shaped. A coil antenna suitable for use as primary antenna 150 may have any number of windings, e.g. 4, 8, 10, 12, 15, or more. A coil antenna suitable for use as primary antenna 150 may have a wire diameter between about 0.01 mm and 2 mm. These antenna parameters are exemplary only, and may be adjusted above or below the ranges given to achieve suitable results.

As previously noted, an antenna suitable for use as primary antenna 150 may include an antenna structured similarly to antenna 152 and may be configured, for example, to include structures as illustrated in FIG. 11*a* and/or 11*b*.

In some embodiments, primary antenna 150 may include a winding height of between 10 and 500 microns (e.g., 20, 30, 55, 70, 110 microns, etc.) and may have a width of between 10 to 500 microns (e.g., 20, 30, 65, 110 microns, etc.). Further, the distance between windings in primary antenna 150, in some embodiments, may be between 0.01 to 1 mm (e.g., 0.1, 0.4, 0.7 mm, etc.).

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158*a*, 158*b*, etc. Amplifier 146 may output the amplified signal to primary antenna 150.

External unit 120 may communicate a primary signal on antenna to the antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158*a* and 158*b*.

Figure 6:
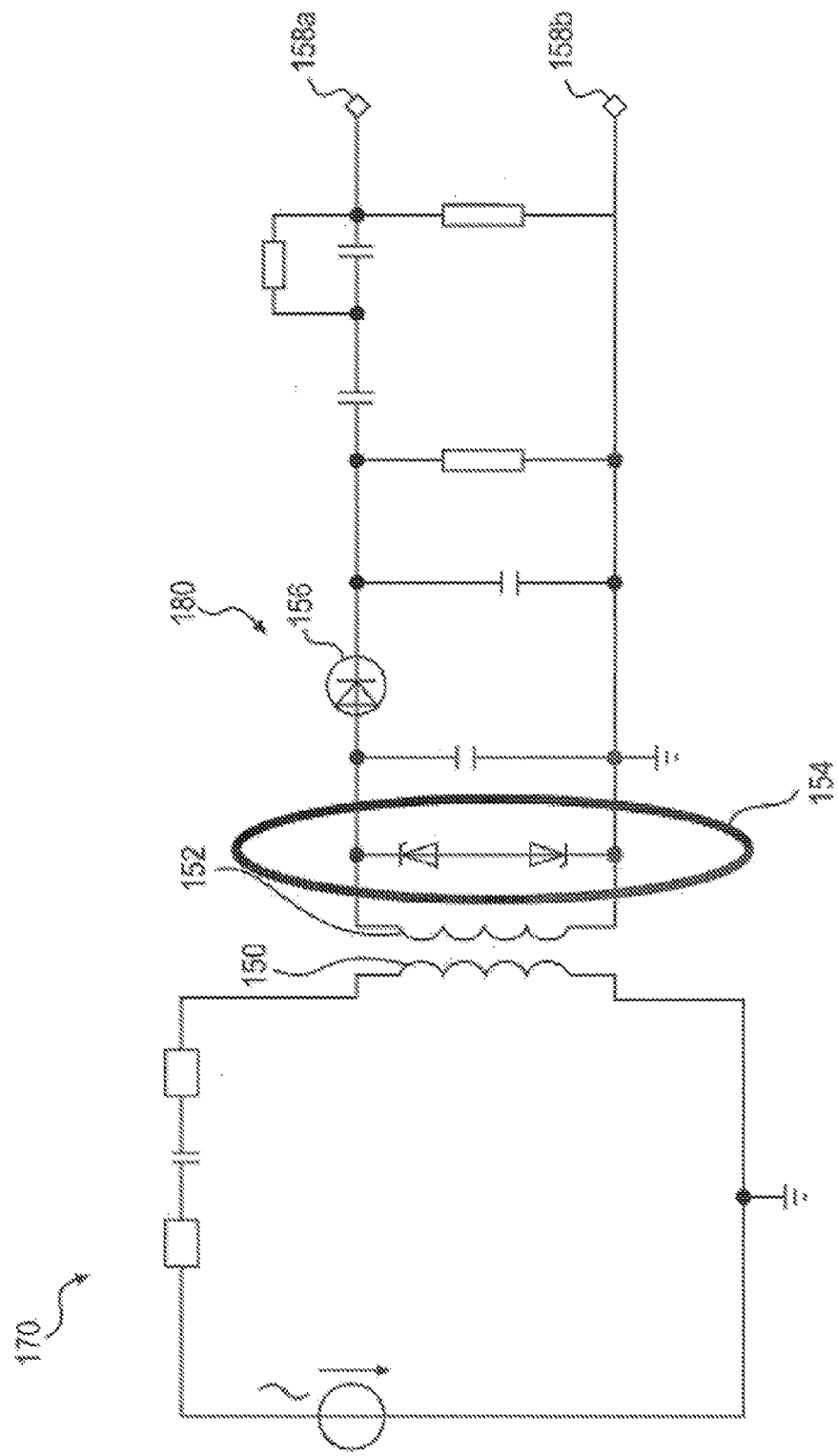
FIG. 6 illustrates circuitry of an implant unit and an external unit, according to an exemplary embodiment of the present disclosure.

FIG. 6 illustrates circuitry 170 that may be included in external unit 120 and circuitry 180 that may be included in implant unit 110. Additional, different, or fewer circuit components may be included in either or both of circuitry 170 and circuitry 180. As shown in FIG. 6, secondary antenna 152 may be arranged in electrical communication with implant electrodes 158*a*, 158*b*. In some embodiments, circuitry connecting secondary antenna 152 with implant electrodes 158*a* and 158*b* may cause a voltage potential across implant electrodes 158*a* and 158*b* in the presence of a secondary signal on secondary antenna 152. This voltage potential may be referred to as a field inducing signal, as this voltage potential may generate an electric field between implant electrodes 158*a* and 158*b*. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In some embodiments, a head pain management, including a sleep apnea treatment device, may include carrier 161 configured to be implanted in a body of a subject with first portion 162a disposed substantially beneath a hairless region of a head of the subject. Electrodes 158a, 158b may be disposed in carrier 161 in a vicinity of at least the occipital nerve and the trigeminal nerve beneath the skin of the subject and in a substantially haired region of the patient's head. Electrodes 158a, 158b may be configured to modulate the occipital and the trigeminial nerves of the subject and decrease or eliminate the sensation of pain.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a treatment device may be configured for implantation in a blood vessel in proximity to at least a renal nerve, a baroreceptor, and a glossopharyngeal nerve of a subject to affect the blood pressure of the subject. In one embodiment, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator placed in a renal artery may receive a modulation control signal tailored to cause an inhibiting or blocking signal at the electrodes, thereby inhibiting a signal to raise blood pressure carried from the renal nerves to the kidneys.

In some embodiments a hypertension therapy device for affecting blood pressure may include a sleep apnea treatment implant configured to be implanted in a blood vessel of a subject in proximity to at least a renal nerve, a baroreceptor, and a glossopharyngeal nerve. Electrodes 158a, 158b may be disposed on the implant and configured to modulate nerve fibers of the subject. Additionally antennas 150, 152 may be disposed on a substrate on the implant.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 7:
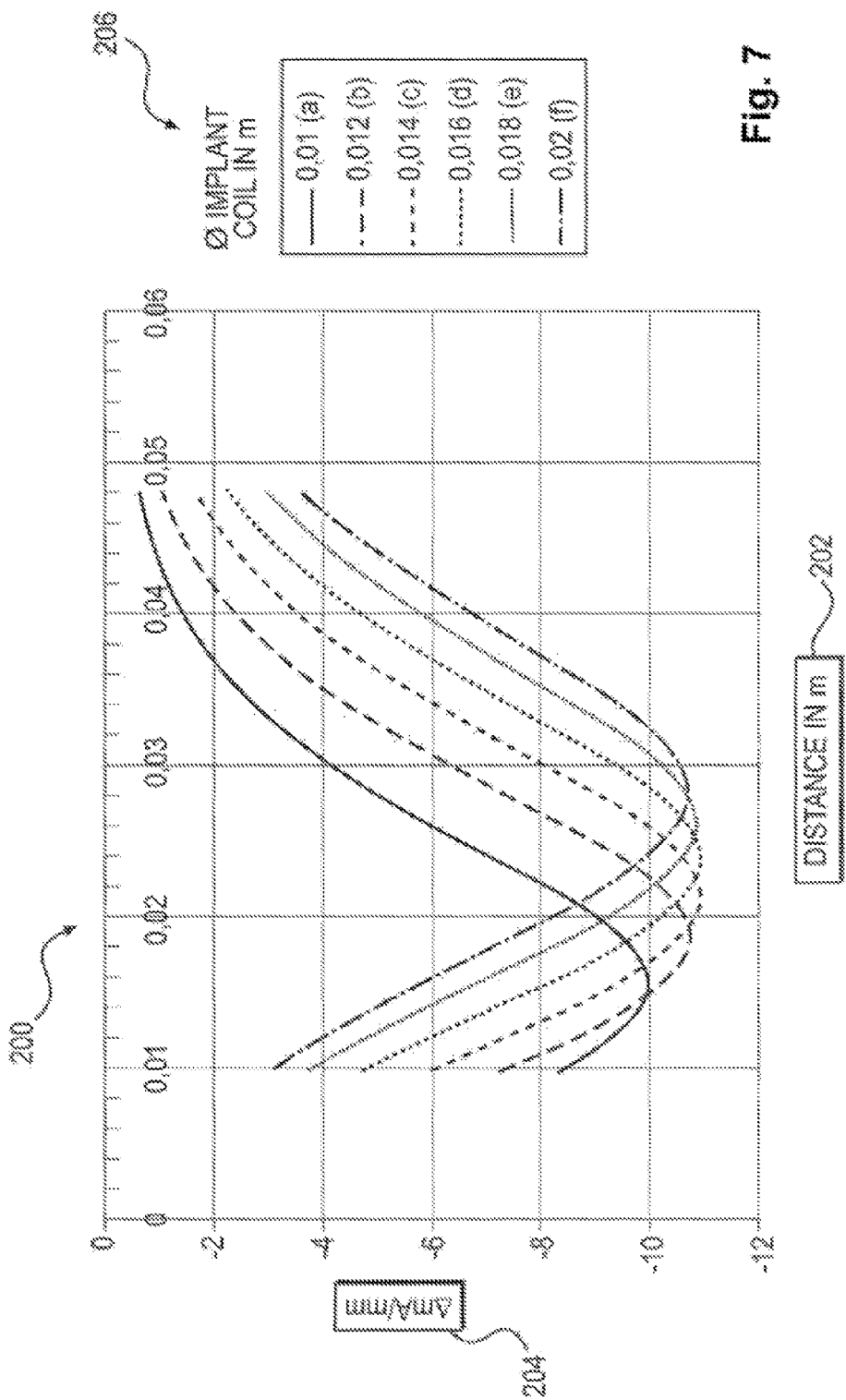
FIG. 7 illustrates a graph of quantities that may be used in determining energy delivery as a function coupling, according to an exemplary disclosed embodiment.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, the non-linear behavior of circuitry 180 in implant unit 110 may be monitored to determine a degree of coupling. For example, the presence, absence, magnitude, reduction and/or onset of harmonic components in the primary coupled signal component on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate at multiple frequencies. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary coupled signal component present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode. Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
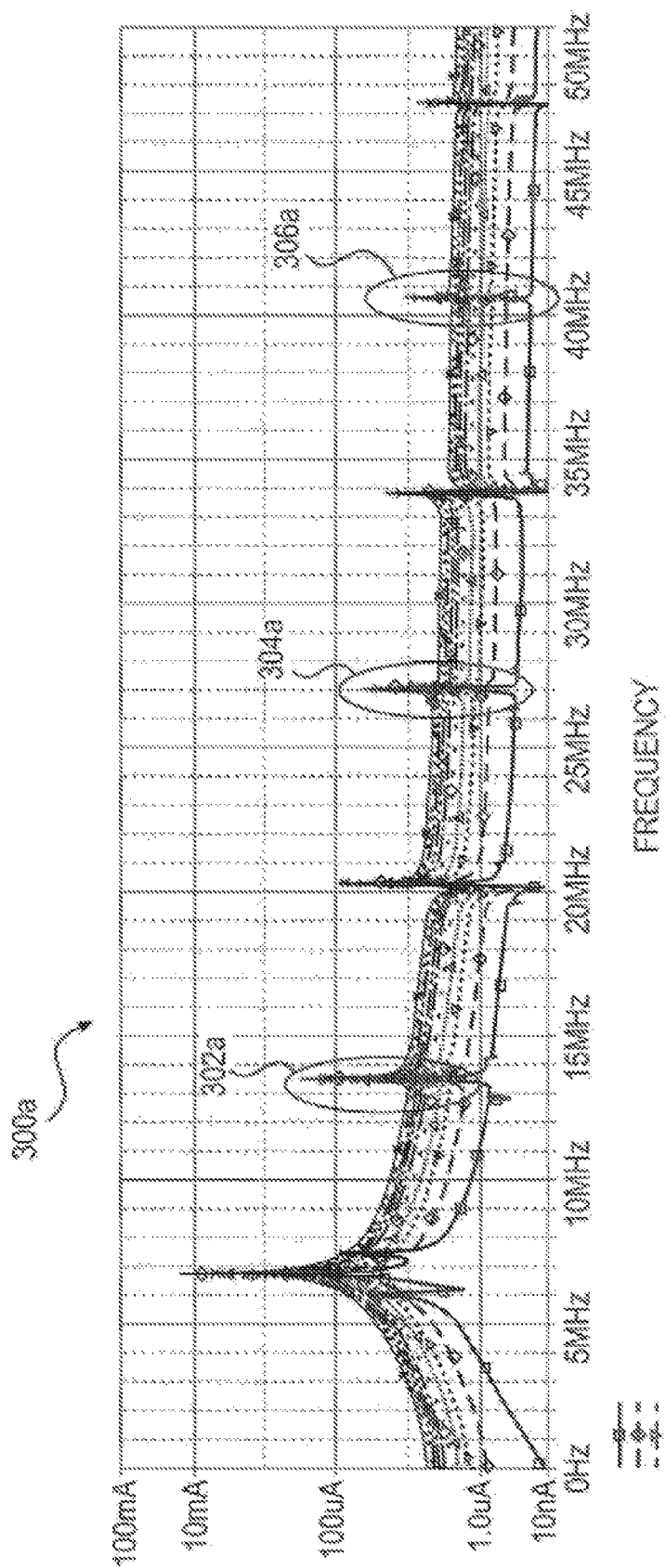
FIG. 8 depicts a graph illustrating non-linear harmonics.
Figure 9:
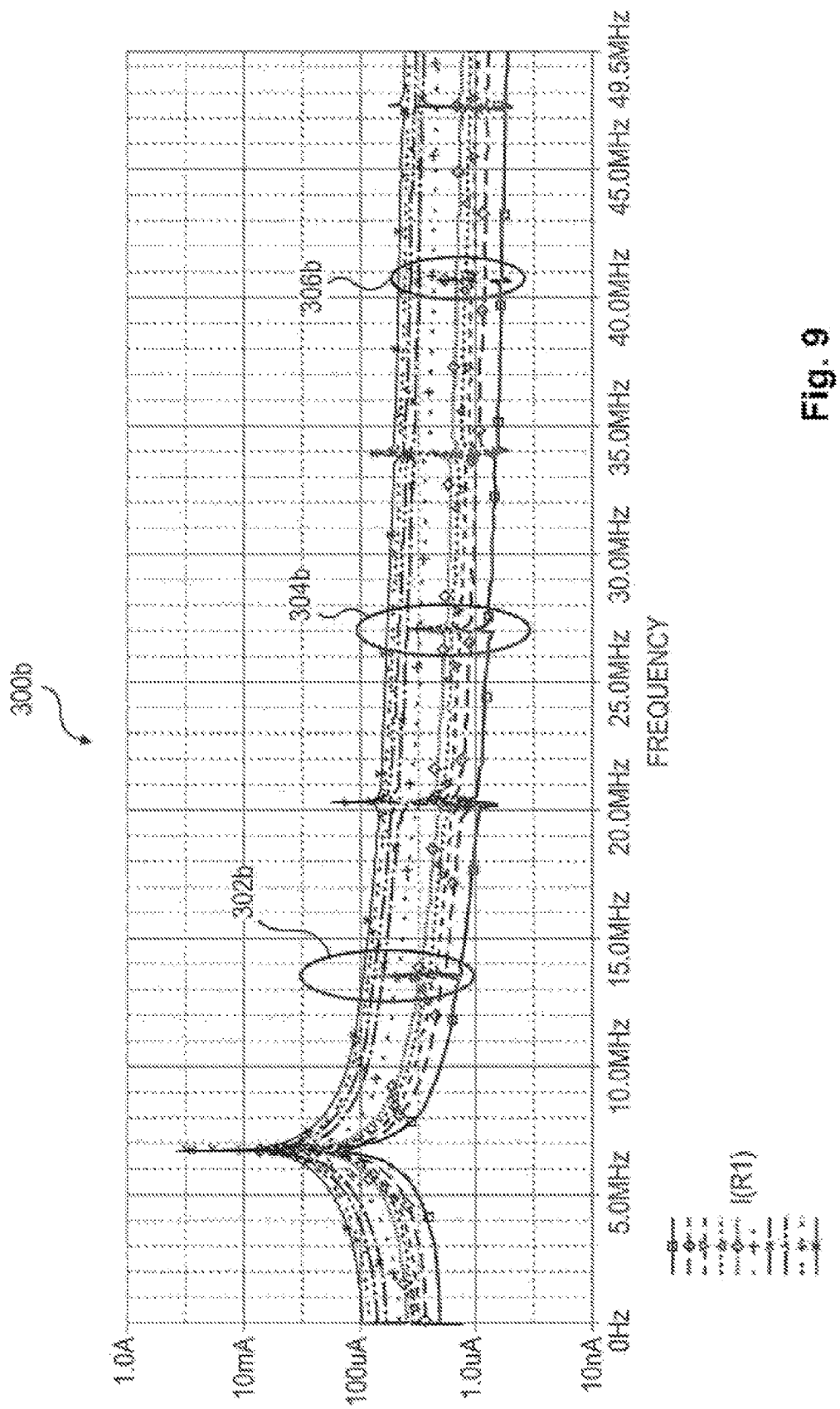
FIG. 9 depicts a graph of quantities that may be used in determining energy delivery as a function coupling, according to an exemplary disclosed embodiment.

FIGS. 8 and 9 illustrate this effect. For example, FIG. 8 illustrates a graph 300*a* that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302*a*), four times the excitation frequency (peak 304*a*) and six times the excitation frequency (peak 306*a*). As the amplitude of the excitation signal rises between 10 nanoamps and 40 microamps, the amplitude of peaks 302*a*, 304*a*, and 306*a* all increase.

FIG. 9 illustrates the effect on the even harmonic response of circuitry 180 caused by harmonics modifier circuit 154. FIG. 9 illustrates a graph 300*b* that shows the oscillatory behavior of circuitry 180 at several amplitudes ranging from about 30 microamps to about 100 microamps. As in FIG. 8, FIG. 9 shows a primary excitation frequency at about 6.7 MHz and second, fourth, and sixth order harmonics (peaks 302*b*, 304*b*, and 306*b*, respectively) appearing at even multiples of the excitation frequency. As the amplitude of the excitation signal rises, however, between about 30 microamps to about 100 microamps, the amplitudes of peaks 302b, 304b, and 306b do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary coupled signal component on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These Figures illustrate data based around a 6.7 MHz excitation frequency. These principles, however, are not limited to the 6.7 MHz excitation frequency illustrated, and may be used with a primary signal of any suitable frequency.

In some embodiments, the determined amplitude of the primary signal corresponding to the transition level of the Zener diodes (which may be referred to as a primary signal transition amplitude) may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also be configured to monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also be configured to determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling) between primary antenna 150 and secondary antenna 152. In other embodiments, processor 144 may be configured to calculate a degree of coupling based on performance characteristics of known circuit components.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g, during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough energy may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of energy in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g, if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g, movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of energy than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g, whether the patient is snoring), by how much the tongue is moving or vibrating, the direction of motion of the tongue, the rate of motion of the tongue, etc.

In response to any of these determined physiologic data, processor 144 may regulate delivery of energy to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering energy to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver energy and wait to determine if the tongue clears on its own. Alternatively, processor 144 may deliver a small amount of energy to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may be configured to use the physiologic data to determine an amount of energy to be delivered to implant unit 110 in order to modulate nerves associated with the tongue with the appropriate amount of energy.

The disclosed embodiments may be used in conjunction with a method for regulating delivery of energy to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of energy from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

Other embodiments of the present disclosure will be apparent to those skilled in the art from consideration of the specification and practice of the present disclosure.

What is claimed is:

1. A medical device, comprising:
    a flexible carrier configured to be implanted in a body of a subject;
    at least one electrode disposed on the flexible carrier, the at least one electrode being configured to modulate nerve fibers of the subject;
    a flexible antenna disposed on the flexible carrier, the flexible antenna electrically connected to the at least one electrode in a manner permitting at least some energy received by the flexible antenna to be transferred to the at least one electrode, the flexible antenna including:
    at least a first conductive trace arranged on a first side of the flexible carrier, the at least a first conductive trace defining at least a first elongated space between portions thereof; and
    at least a second conductive trace arranged on a second side of the flexible carrier, the at least a second conductive trace defining at least a second elongated space between portions thereof,
    wherein the at least a first conductive trace is at least partially offset from the at least a second conductive trace such that portions of the first conductive trace overly the at least a second elongated space and wherein portions of the second conductive trace underlay the at least a first elongated space,
    wherein the first conductive trace includes first windings and at least some of the first windings are connected to one another by first electrical trace steps, the second conductive trace includes second windings and at least some of the second windings are connected to one another by second electrical trace steps, and one or more of the first electrical trace steps cross one or more of the second trace steps at a non-zero angle.

2. The medical device of claim 1, wherein the antenna and carrier are encapsulated within a flexible polymeric coating.

3. The medical device of claim 1, wherein the first conductive trace and the second conductive trace each includes a coil, and the first elongated space and the second elongated space include areas between windings of the coils of the first and second conductive traces.

4. The medical device of claim 3, wherein the coils of the first and second conductive traces include rectangular windings.

5. The medical device of claim 3, wherein the coils of the first and second conductive traces include oval-shaped windings.

6. The medical device of claim 3, wherein the coils of the first and second conductive traces include circular windings.

7. The medical device of claim 1, wherein the first conductive trace and the second conductive trace are electrically connected via a trace extending through the flexible carrier.

8. The medical device of claim 1, wherein the flexible antenna includes a ferrite core.

9. The medical device of claim 1, wherein the flexible carrier includes a dielectric material.

10. The medical device of claim 1, wherein the first conductive trace and the second conductive trace each include a coil, and the coils of the first and second conductive traces have a diameter of between 0.5 mm and 30 mm.

11. The medical device of claim 1, wherein the flexible antenna is configured to conform to contours of tissue in the body of the subject.

12. The medical device of claim 1, wherein the first conductive trace overlies the at least a second elongated space and wherein the second conductive trace underlays the at least a first elongated space.

13. The medical device of claim 1, wherein the flexible antenna further includes at least a third conductive trace spaced apart from the second conductive trace by an insulating layer.

14. The medical device of claim 1, wherein at least portions of the flexible carrier, the at least one electrode, and the flexible antenna are covered with an encapsulation structure including a layer of parylene and a layer of silicone.

* * * * *

UNITED STATES PATENT AND TRADEMARK OFFICE
CERTIFICATE OF CORRECTION

PATENT NO. : 9,220,908 B2  
APPLICATION NO. : 14/496212  
DATED : December 29, 2015  
INVENTOR(S) : Adi Mashiach Page 1 of 1

It is certified that error appears in the above-identified patent and that said Letters Patent is hereby corrected as shown below:

On The Title Page, Item (57) Abstract, line 19, "conductive trace overly the at least" should read -- conductive trace overlay the at least --.

In The Claims

Claim 1, col. 27, lines 31-32, "conductive trace overly the at least" should read -- conductive trace overlay the at least --.

Signed and Sealed this  
Third Day of May, 2016

Michelle K. Lee  
*Director of the United States Patent and Trademark Office*